US006988497B2

(12) United States Patent
Levine

(10) Patent No.: US 6,988,497 B2
(45) Date of Patent: Jan. 24, 2006

(54) APPARATUS FOR EQUALIZING AIR PRESSURE IN AIR RESPIRATORY SYSTEM

(75) Inventor: Walter Levine, Lincolnwood, IL (US)

(73) Assignee: Medex Cardio-Pulmonary, Inc., Carlsbad, CA (US)

( * ) Notice: Subject to any disclaimer, the term of this patent is extended or adjusted under 35 U.S.C. 154(b) by 74 days.

(21) Appl. No.: 10/246,153

(22) Filed: Sep. 18, 2002

(65) Prior Publication Data

US 2004/0050386 A1 Mar. 18, 2004

(51) Int. Cl.
*A61M 16/00* (2006.01)

(52) U.S. Cl. .......................... 128/203.27; 128/203.17; 128/203.26; 128/204.14; 128/204.17; 261/127; 261/142; 392/386; 392/391; 392/432

(58) Field of Classification Search ........ 604/403–416; 128/200.14–200.24, 203.12, 203.15, 203.16, 128/203.17, 203.23, 203.26, 204.17, 204.18
See application file for complete search history.

(56) References Cited

U.S. PATENT DOCUMENTS

| 4,110,419 | A | * | 8/1978 | Miller | 261/142 |
|---|---|---|---|---|---|
| 4,195,044 | A | * | 3/1980 | Miller | 261/142 |
| 4,708,831 | A | | 11/1987 | Elsworth et al. | |
| 4,773,410 | A | | 9/1988 | Blackmer et al. | |
| 4,883,049 | A | | 11/1989 | McDonald | 128/202.22 |
| 4,926,856 | A | | 5/1990 | Cambio, Jr. et al. | |
| 5,172,686 | A | | 12/1992 | Anthony | |
| 5,195,515 | A | | 3/1993 | Levine | |
| 5,390,665 | A | | 2/1995 | Leach | |
| 5,640,951 | A | * | 6/1997 | Huddart et al. | 128/204.17 |
| 5,769,071 | A | | 6/1998 | Turnbull | |
| 5,897,526 | A | * | 4/1999 | Vaillancourt | 604/82 |
| 5,943,473 | A | * | 8/1999 | Levine | 392/401 |
| 6,102,037 | A | | 8/2000 | Koch | |
| 6,349,722 | B1 | * | 2/2002 | Gradon et al. | 128/203.17 |
| 6,367,472 | B1 | * | 4/2002 | Koch | 128/203.12 |

FOREIGN PATENT DOCUMENTS

| GB | 2126102 | | 3/1984 | |
|---|---|---|---|---|
| JP | 10-141715 | * | 5/1998 | 128/203.15 |

* cited by examiner

Primary Examiner—Glenn K. Dawson
(74) Attorney, Agent, or Firm—Wood, Herron & Evans, LLP

(57) ABSTRACT

A humidifier apparatus for operating at an air pressure is disclosed for use with a respiratory therapy breathing apparatus that provides a breathable gas supply to patients requiring higher concentrations of liquid vapor and gas pressure. The humidifier apparatus includes a feed liquid supply bag in fluid communication with a humidifier cartridge via a conduit. The conduit enables air to flow therethrough to equalize air pressure between the humidifier cartridge and the feed liquid supply bag in response to liquid being supplied to the humidifier cartridge.

40 Claims, 4 Drawing Sheets

APPARATUS FOR EQUALIZING AIR PRESSURE IN AIR RESPIRATORY SYSTEM

BACKGROUND OF THE INVENTION

The present invention relates generally to respiratory devices, and more particularly to humidifier devices delivering to a patient gases that have a controlled vapor level and temperature.

When a healthy person breathes atmospheric air, the air passages of the person supply heated moisture to the inhaled gases, and the person's body generates the required amount of heat and moisture to satisfy the individual's respiratory needs. However, for patients that fail to satisfy their respiratory needs by breathing from the ambient environment (e.g., unhealthy children needing a higher concentration of water vapor in their breathable air), it becomes necessary to supply additional water to a humidifier chamber of an optionally heated humidifier device to achieve an elevated moisture concentration level in the patient's breathable air.

Known systems for providing heated and moisturized respiratory gases to patients basically fall into two groups: nebulizers, which produce aerosols of fine water droplets; and heated humidifiers, which supply heat and moisture to a gas by the passage of the gas through or over a heated water bath or evaporated surface. The present invention is directed to heated humidifiers.

One such humidifier system includes a rigid, refillable water container designed to be placed upon a base unit having a heating element and is disclosed in U.S. Pat. No. 5,195,515 to Levine, which is herein incorporated by reference. This system includes a disposable heated cartridge humidifier for use with a collapsible water supply container and a heating device. The cartridge housing has a base plate fabricated from a conductive material such as metal, preferably aluminum.

Another known humidifier system having a gravity feed collapsible water supply bag is disclosed in U.S. Pat. No. 5,943,473 also to Levine, which is herein incorporated by reference. This system includes a humidifier cartridge for engaging a heating unit. The humidifier cartridge has a water inlet adapted to be connected to the gravity feed bag and is in fluid communication with a chamber of the humidifier cartridge.

One problem with known humidifiers using gravity feed collapsible water supply bags is that these water supply bags cannot supply water to the humidifier chamber during the feeding of water to the humidifier chamber, when increased air pressure within the humidifier chamber exceeds the air pressure in the water supply bags. This higher air pressure in the humidifier chamber inhibits water flow from the water supply bag to the humidifier chamber, resulting in humidifier devices that deliver to patients insufficient breathable gas supplies having controlled vapor levels and temperatures.

SUMMARY OF THE INVENTION

A humidifier apparatus configured for operating at an air pressure includes a feed liquid supply bag for use in a respiratory therapy circuits. The humidifier provides a breathable gas supply (e.g., high water concentration gas supply) to patients using a humidifier cartridge that receives a liquid supply from the feed liquid supply bag. A conduit is in fluid communication with the humidifier cartridge and the feed liquid supply bag, and equalizes air pressure there between. In particular, the conduit allows air to flow to the feed liquid supply bag in response to liquid flowing to the humidifier cartridge, thereby compensating for any liquid exiting from the feed liquid supply bag. In one embodiment, the conduit is integrally formed with the feed liquid supply bag.

DETAILED DESCRIPTION OF THE INVENTION

A humidifier apparatus includes a housing having an air pressure equalizing conduit that extends from the housing to a gravity feed liquid supply bag and promotes the supply of liquid, e.g., sterile water, to the housing. The housing also has inlets for receiving breathable gases and liquid, and outlets for providing the humidified gases to patients and returning air to the gravity feed liquid supply bag. In particular, the housing includes a top portion having a breathable gas inlet, a liquid inlet, a humidifier gas outlet, and an air pressure equalizing outlet. A separate heating element provides the heat required to evaporate the liquid and humidify the breathable gases passing through the housing. A base plate of the housing engages the heating element. The base plate includes a central heat conductive portion and an outer insulating portion to prevent a dissipation of heat generated by the heat source to a sidewall of the housing.

Figure 1:
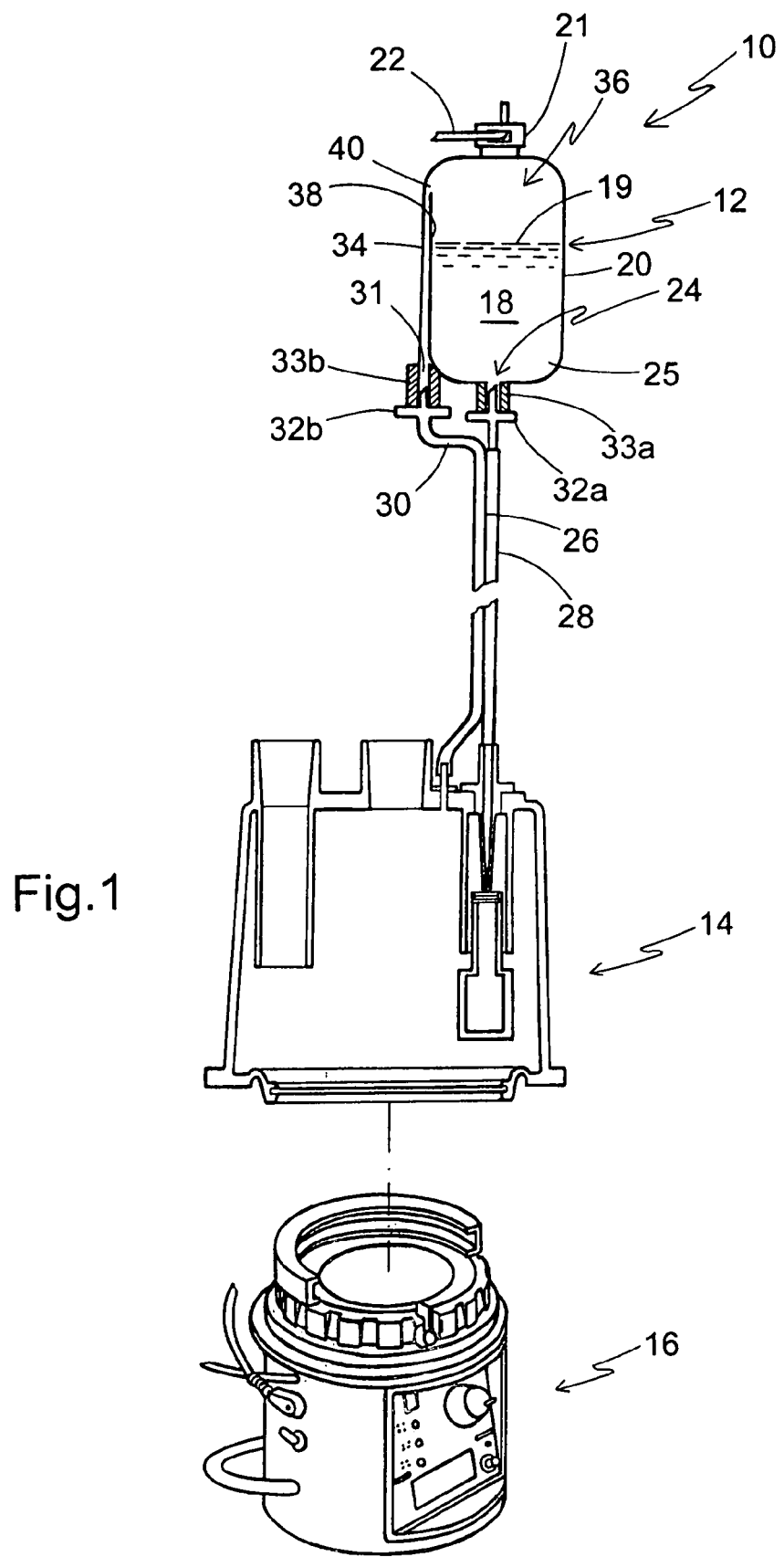
FIG. 1 is a fragmentary sectional view of a humidifier apparatus, suitable for use with, and incorporating the present pressure equalizing apparatus and shown exploded from a heater.

Referring now to FIG. 1, the humidifier apparatus for use in a respiratory therapy breathing apparatus (not shown) having a breathable gas supply and operating at an atmospheric pressure is shown and generally designated as 10, and includes a liquid supply system 12. The liquid supply system 12 is in fluid communication with a humidifier cartridge 14, such as a heated humidifier cartridge, that is configured for operationally engaging with a heating unit, generally designated as 16. Sterile liquid 18 is contained up to an internal liquid level 19 within a liquid supply bag 20 that feeds the liquid to the humidifier cartridge 14. In one embodiment, the bag 20 can be a gravity feed, collapsible water supply bag. It is contemplated that the bag 20 is preferably blow molded or alternatively formed from two or more panels (not shown) that are sealed together to form a container for storing the sterile liquid 18. The bag 20 may include a hanging eyelet 21 for suspension at a specified height by a hanger 22 that passes through the eyelet, as is known in the healthcare field.

A tubular, depending liquid delivery outlet 24 is located at a lower end 25 of the bag 20 and feeds liquid via gravity to a conduit 26 that includes a pair of feed lines, and more particularly a liquid feed line 28 and an air return line 30. The air return line 30 feeds air from the humidifier cartridge 14 to the bag 20 via a depending air delivery outlet 31. In a preferred embodiment, a pair of piercing pins 32a, 32b (best seen in FIG. 5) control fluid flow from the bag 20 to the humidifier cartridge 14 and vice-versa. Securing sleeves 33a, 33b provide support for the piercings of the bag 20 by the piercing pins 32a, 32b. However, it is contemplated for other embodiments of the humidifier apparatus 10 that the piercing pins 32a, 32b and the securing sleeves 33a, 33b can be eliminated from the humidifier apparatus 10 to have the conduit 26 directly connected to the bag 20.

The conduit 26 may be formed of a flexible, transparent plastic material, of the type commonly used in the respiratory care industry, and can be configured for having a portion 34 of the air return line 30 feed into an uppermost portion 36 of the bag 20 above the internal liquid level 19 of the liquid 18. That is, the portion 34 may be connected to a wall 38 of the bag 20 and feed into the uppermost portion 36 via an opening 40. Preferably, the air return line 30 is fed to the bag 20 above the liquid line 19. The conduit 26 is preferably formed of a pair of feed lines that are separated from one another, or alternatively partially joined to minimize operator entanglement with the conduit during use of the apparatus 10. In particular, the conduit 26 is configured for passing liquid through the feed line 28 and air through the return line 30. The flow of liquid through the conduit 26 can be continuous, or intermittent depending on the desired amount of liquid 18 to be supplied to the humidifier cartridge 14.

A key feature of the present invention is that the flow of air is unobstructed between the bag 20 and the humidifier cartridge 14 to equalize air pressure between the bag and the humidifier cartridge as the liquid 18 is dispensed from the bag. That is, the conduit 26 equalizes air pressure between the humidifier cartridge 14 and the bag 20 independent of the flow of liquid 18 from the bag. In addition, it is preferable to have the air return line 30 feed air near or at the uppermost portion 36 of the bag 20 to prevent liquid flow into the humidifier cartridge 14 via the air return line.

Figure 2:
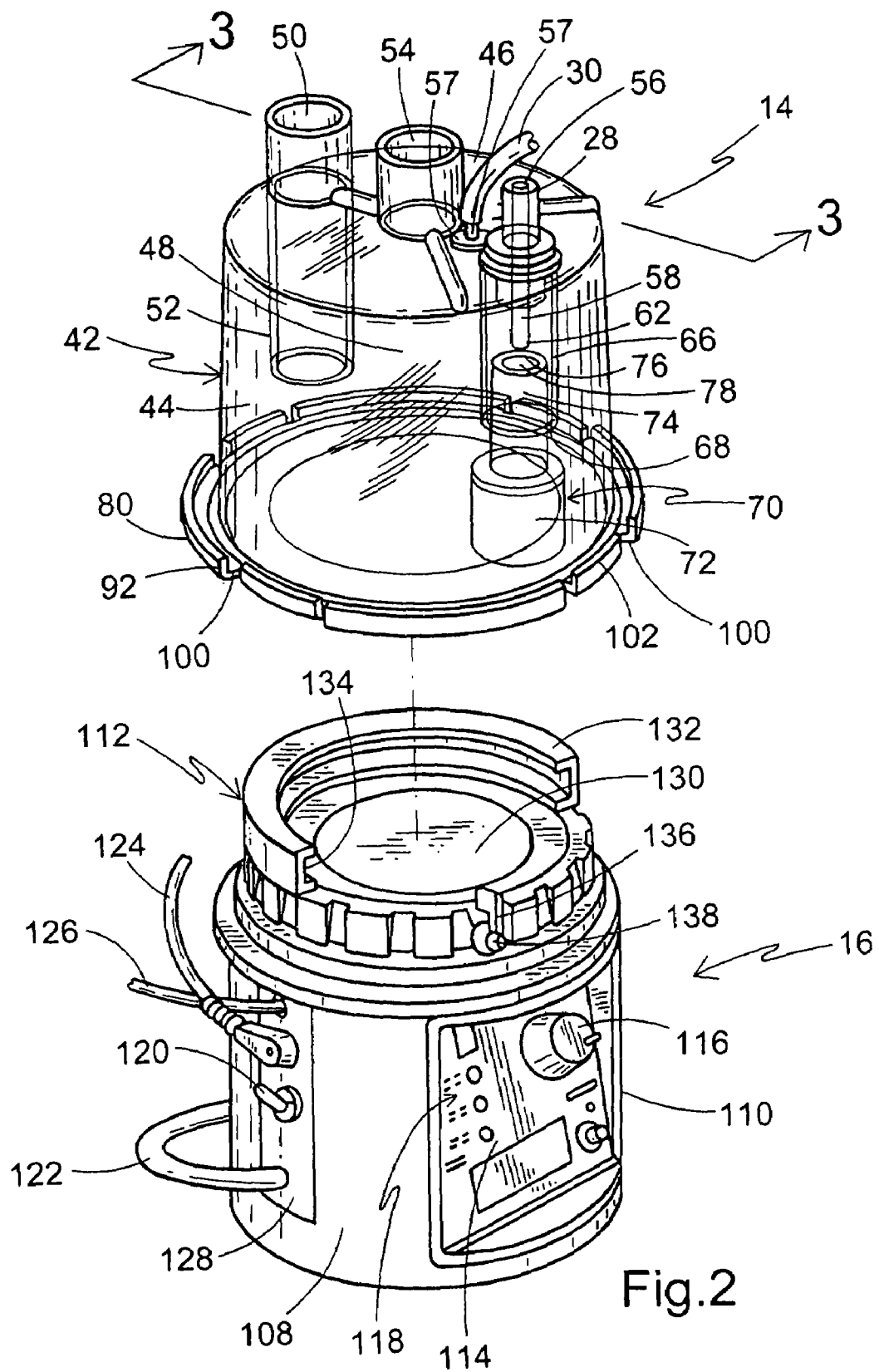
FIG. 2 is partially exploded perspective view of the humidifier cartridge and heat source of FIG. 1, with some parts omitted for clarity.
Figure 3:
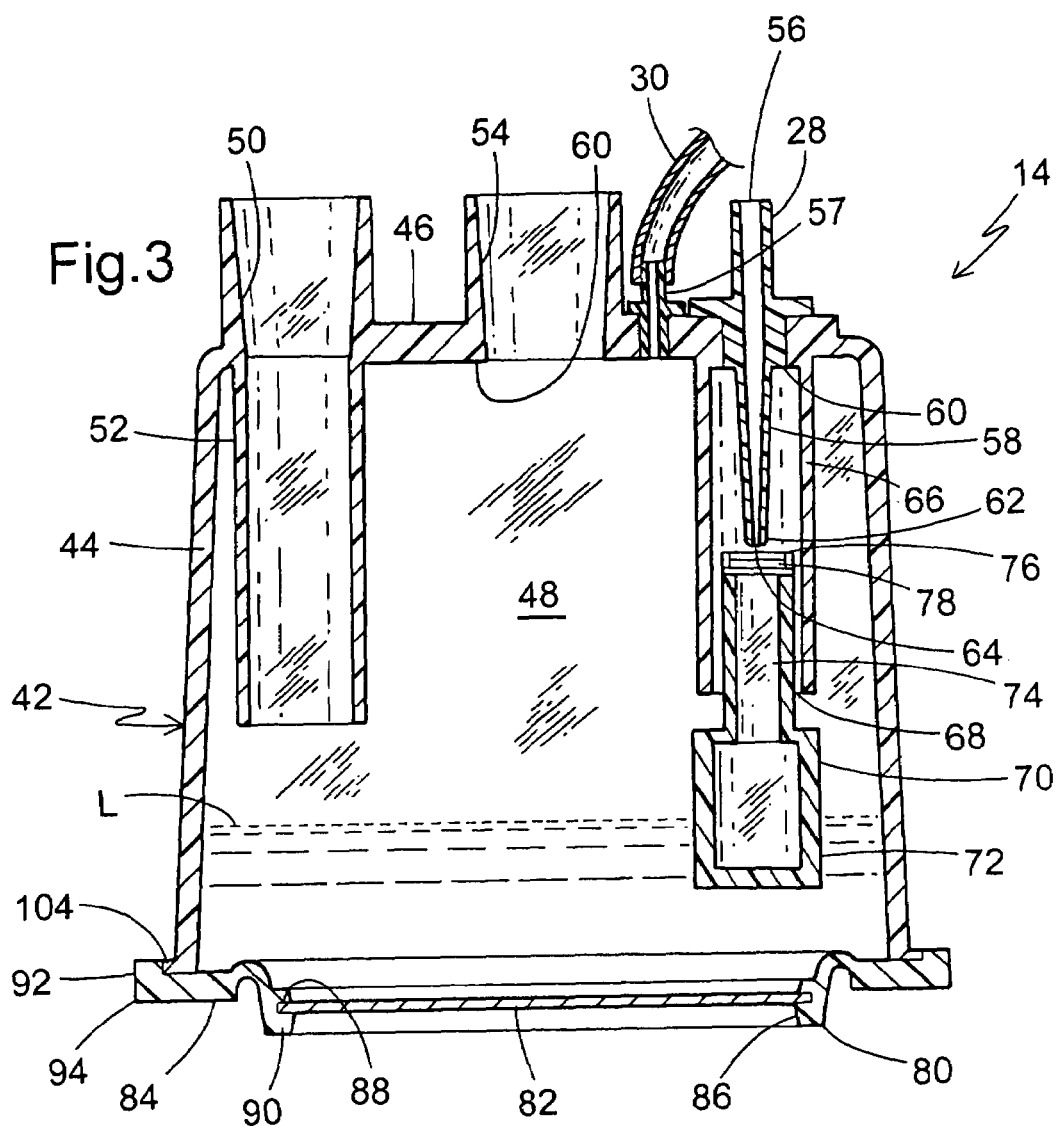
FIG. 3 is a cross-section taken along the line 3—3 of FIG. 2 and in the direction generally indicated.

Referring now to FIGS. 2 and 3, the humidifier cartridge 14 includes a humidifier housing 42 with a substantially vertical sidewall 44 and a top portion 46 integrally formed with the vertical sidewall to define a humidifier chamber 48. Extending above and below the top portion 46 is a substantially cylindrical gas inlet 50 with a lower end 52. Appending from the top portion 46 is a substantially cylindrical gas delivery outlet 54. The gas inlet 50 and the gas delivery outlet 54 are configured to be connected to a breathable gas delivery system of the type used for respiratory patients. A liquid inlet port 56, appending from the top portion 46, is configured to be connected to the gravity feed collapsible liquid supply bag 20 via the liquid feed line 28. The gas inlet 50, the gas delivery outlet 54, and the liquid inlet 56 are in fluid communication with the chamber 48.

An air or pressure equalizing outlet 57, appending from the top portion 46 and in fluid communication with the chamber 48, is configured to be connected to the air return line 30. The air outlet 57 is positioned, relative to the chamber 48, at or above the liquid inlet 56 and permits a free flow of air between the chamber and the bag 20 to equalize air pressure therebetween. Air flows through the air outlet 57 in response to liquid 18 flowing via the conduit 26 into the chamber 48, and can be continuous or intermittent. The air outlet 57 can be formed of any type of connecting member that provides a path for air flow from the chamber 48 to the air return line 30, as is known in the art. An advantage of locating the air outlet 57 in the top portion 46 of the housing 42 is that air pressure is continuously equalized even if liquid is flowing into the heated cartridge humidifier 14.

In different embodiments, the humidifier housing 42 can be made of various plastics. However, it is contemplated that other types of conventionally available self-supporting, sanitizable, and inexpensive materials may be used to fabricate at least a portion of the housing 42. Also, while it is preferred that the inlets 50 and 56, and the outlet 54 are disposed on the top portion 46, it is also contemplated that these features may be located elsewhere on the housing 42, such as on the sidewall 44.

It is preferred that the liquid inlet 56 is in fluid communication with a liquid feed tube 58 depending from an underside 60 of the top portion 46. A lower end of the feed tube 58 includes a nipple formation 62 with an axially disposed opening 64. A float retaining tube 66 depends from the underside 60 of the top portion 46 and circumscribes the liquid feed tube 58. The float retaining tube 66 includes a lower opening 68.

A float 70 is dimensioned to be slidingly retained in the float retaining tube 66. The float 70 is essentially a tube of liquid tight buoyant material with a larger diameter lower end 72. A top portion 74 of the float 70 has a relatively smaller diameter than the lower end 72 and has a recess 76 into which a disc or pad 78 of rubber or other resilient material is secured. The dimensions and material used for the pad 78 are such that upon contact with the nipple formation 62, the axial opening 64 will be sealed, effectively cutting off the flow of liquid from the liquid inlet 56.

Figure 4:
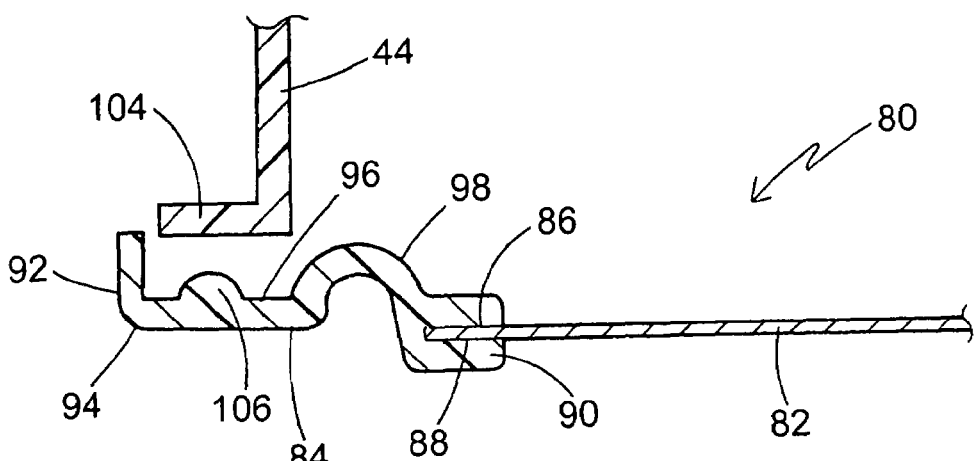
FIG. 4 is a fragmentary vertical cross-sectional view of the base plate for the present humidifier cartridge.

Referring now to FIGS. 3 and 4, the housing 42 is seated on a base plate 80 which includes a central conductive portion 82 and an insulating outer portion 84. A perimeter 86 of the central conductive portion 82 is sealingly retained within a groove 88 at an inner diameter 90 of the insulating portion 84. The central conductive portion 82 is preferably made of anodized aluminum but, it is contemplated that other similar heat conductive materials would be equally useful. In the preferred embodiment, the conductive portion 82 is insert molded into the insulating portion 84. However, it is contemplated that alternative production techniques known to skilled practitioners may be utilized.

A peripheral lip 92 extends vertically from an outer diameter 94 of the insulating portion 84. The insulating portion 84 is made of a plastic material. Between the inner diameter 90 and the outer diameter 94 is disposed an annular mating surface 96 and an annular, generally arcuately shaped support formation 98. As best seen in FIG. 2, the peripheral lip 92 is interrupted in a plurality of positions about the outer diameter 94 to form recesses or notches 100. The notches 100 include notch lips 102 which are essentially the same height as peripheral lips 92 but are positioned closer to the mating surface 96 than to the peripheral lip 92. In operation, the notches 100 are used for properly engaging the cartridge 14 to the heating unit 12.

Referring again to FIG. 4, the lower end of the sidewall 44 of the housing 42 has a radially projecting flange 104 which forms the attachment point for the base plate 80. The flange 104 is interrupted in a plurality of positions by the notches 100 on the outer diameter 94 of the insulating portion 84. The mating surface 96 of the insulating portion 84 includes a plurality of knobs 106 spaced about the base plate 80. Once the flange 104 is seated on the mating surface 96, the mating surface and the flange are preferably ultrasonically welded together. The knobs 106 provide sufficient material to form an absolute bond between the flange 104 and the surface 96. However, it is also contemplated that suitable chemical adhesives may alternatively be used to sealingly fasten the base plate 80 to the housing 42.

Structural support is provided to the base plate 80 by the support formation 98. In addition, the arcuate shape of the support formation 98 exerts a preload or hold down force on the conductive portion 82, which holds the conductive portion down against the heating unit 12.

Referring now to FIG. 2, the heating unit 16 is designed to provide heat to the liquid delivered to the chamber 48 through the inlet 56 so that the liquid 18 is more easily vaporized, and to provide liquid to a patient at a temperature which is as comfortable as possible. Included in the heating unit 16 is a housing 108 having a lower end 110 designed for positioning a substrate such as a shelf or a table, and an upper end 112. A control panel 114 is part of the heating unit 16 and is preferably equipped with a temperature setting control 116 and various temperature warning lights and alarm indicators, generally designated as 118. A power switch 120, a power cord 122, and temperature sensor inputs 124 and 126 are preferably located on a panel 128 of the housing 108. It is contemplated that the selection and arrangement of components for the heater 16 may vary to suit the application. The upper end 112 of the housing 108 has a heating surface 130 which is partially surrounded by a generally semicircular bracket 132. The bracket 132 is generally "C" or channel shaped in cross section to define an inwardly opening channel 134. A pivoting locking tab 136 is mounted to the upper end 112 of the housing 108 through use of a pivot member 138, which may be a pin or threaded fastener. The dimensions of the peripheral lip 92 and notch lips 102 of the base plate 80 are such that the humidifier cartridge 14 may be slid into the channel 134 to engage the bracket 132. The locking tab 136 is then moved to the vertical position as indicated in FIG. 1 to maintain the humidifier 14 in operational alignment upon the heating surface 130. In this position, the conductive portion 82 will be conductively heated by the heating surface 130.

In operation, liquid 18 is supplied through the liquid inlet 56 by the gravity feed liquid supply bag 20. As the liquid level 'L' (best seen in FIG. 3) within the chamber 48 rises, the float 70 rises until the disc 78 on the top portion 74 of the float 70 contacts the opening 64 of the feed tube 58 and effectively cuts off the flow of liquid into the housing 42. Breathable gases for treatment of patients enter the housing 42 through the gas inlet 50. The extended lower end 52 of the inlet 50 directs the gases to the area immediately above the surface 'L' of the liquid 18 so that the gas is prevented from directly exiting through the outlet 54 without being properly humidified.

Heat generated by the heating surface 130 is transferred through the conductive portion 82 to heat the liquid 18 in the chamber 48 to vaporize the liquid and warm the gases. As the respiratory gases flow through the heated and humidified chamber 48, the liquid level 'L' will fall due to evaporation. As the liquid level falls, the float 70 will also fall, pulling the disc 78 away from the feed tube opening 64 to allow the lost liquid to be replaced by liquid 18 flowing from the bag 20 and through the liquid feed line 26 to the liquid inlet 56.

Figure 5:
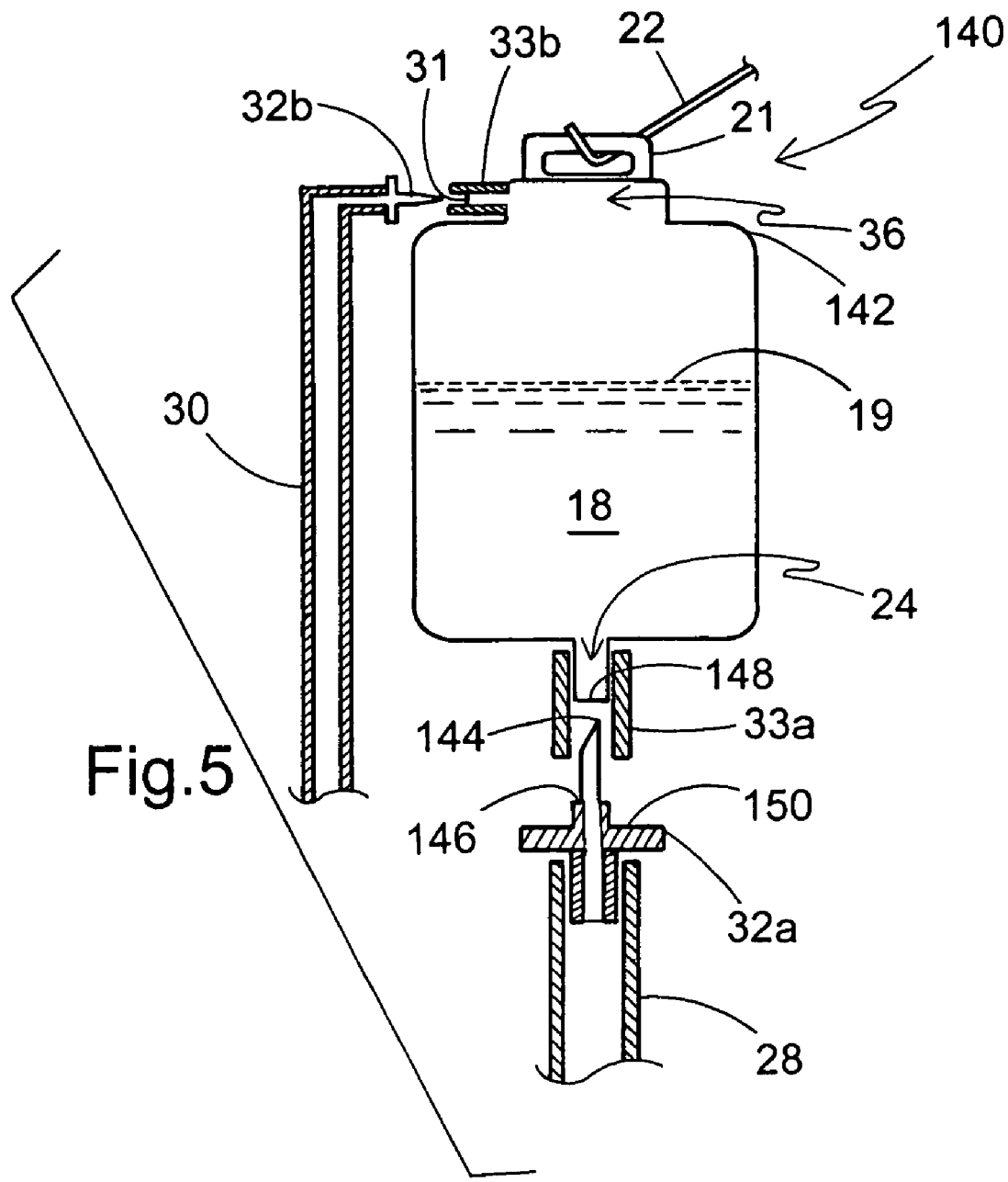
FIG. 5 is a fragmentary vertical cross-sectional view of an alternative embodiment of the liquid supply system.

Turning now to FIG. 5, an alternative embodiment of the liquid supply system 12 of FIG. 1 is generally designated as 140, and includes a feed liquid supply bag 142. FIG. 5 uses reference numerals from FIG. 1 to identify like components. In this embodiment, a portion of the air return feed line 30 is not attached to the bag 142. The liquid securing sleeve 33a facilitates insertion of the piercing pin 32a into the water delivery outlet 24. Similarly, securing sleeve 33b facilitates insertion of the piercing pin 32b into the uppermost portion 36 of the bag 142 to enable air flow into the bag. Optionally, other piercing pins and/or securing sleeves may be provided for other feed lines into the bag 142. The liquid supply bag 20 again can include a hanging eyelet 21 for receiving a hanger 22 that suspends the bag 142. Preferably, the tubular, depending liquid delivery outlet 24 is at least partially enclosed by the securing sleeve 32a that may be connected to the bag 142. The piercing pin 32a has a tip 144 that is configured for piercing the bag 20. In addition, the piercing pin 32a includes a smaller diameter shoulder 146 for abutting in a frictional fit against an end 148 of the liquid delivery outlet 24 and a larger diameter shoulder 150 that also frictionally abuts against the securing sleeve 142 and the liquid feed line 28. In a similar manner, the air feed piercing pin 33b can be attached to the air return line 30 and inserted into the upper portion 36 of the bag 142 at the air delivery outlet 31. The frictional fit ensures that the piercing pins 32a, 32b prevent leakage of liquid 18 from the water delivery outlet 24 and air from the air delivery outlet 31.

It will be appreciated that a major advantage of the present humidifier apparatus 10 depicted in FIG. 1 is that the air outlet 57 in the top portion 46 of the humidifier cartridge 14 enables improved liquid flow from the liquid supply bag 20 to the humidifier cartridge 14. This ensures that a constant supply of liquid 18 is available to humidify the respiratory gases.

An important feature of the present humidifier cartridge 14 is that the air outlet 57, being located at the top portion 46 of the housing 42, provides air pressure equalization between the humidifier cartridge and the bag 20 to prevent possible rupture of the bag. Moreover, equalizing the air pressure enables liquid 18 to flow to the chamber 48 upon the disc 78 moving away from the feed tube opening 64 to allow a flow of liquid to the chamber 48. Under such conditions, the apparatus 10 is able to deliver sufficient breathable gas supplies with humidified levels and temperatures to the respiratory breathing apparatus, and ultimately patients requiring such air.

While a particular embodiment of the humidifier apparatus of the invention has been shown and described, it will be appreciated by those skilled in the art that changes and modifications may be made thereto without departing from the invention in its broader aspects and as set forth in the following claims.

What is claimed:

1. A humidifier apparatus for use in a respiratory therapy circuit having a breathable gas supply and operating at an air pressure, the apparatus comprising:
   a feed liquid supply bag;
   a humidifier cartridge in fluid communication with said feed liquid supply bag for receiving liquid; and
   a conduit for placing said humidifier cartridge in fluid communication with said feed liquid supply bag, said conduit connected to said feed liquid bag to equalize air pressure between said humidifier cartridge and said feed liquid supply bag independent of a flow of liquid from said feed liquid supply bag.

2. The apparatus of claim 1, wherein said conduit comprises a pair of feed lines separately transferring air and liquid between said humidifier cartridge and said feed liquid supply bag.

3. The apparatus of claim 2, wherein one of said feed lines comprises an air return line and the other feed line comprises a liquid feed line.

4. The apparatus of claim 3, wherein said humidifier cartridge includes a chamber configured for receiving liquid fed by said liquid feed line and transferring air in said chamber to said feed liquid supply bag in response to said received liquid.

5. The apparatus of claim 1, wherein said feed liquid supply bag has a sidewall and comprises a collapsible structure that receives air in response to a transfer of liquid from said liquid supply bag to said humidifier cartridge.

6. The apparatus of claim 5, wherein said conduit includes an air return line and a liquid feed line connected to said feed liquid supply bag.

7. The apparatus of claim 6, wherein said feed liquid supply bag is gravity fed and said humidifier cartridge is a heated humidifier cartridge.

8. The apparatus of claim 1, wherein said humidifier cartridge further comprises a housing defining a chamber and having a pressure equalizing outlet therethrough for enabling air to flow between said chamber and said feed liquid supply bag.

9. The apparatus of claim 8, wherein said air outlet is located at a top portion of said housing.

10. The apparatus of claim 1, wherein said humidifier cartridge includes an interior chamber adapted to bold liquid, said interior chamber being selectively exposed to said feed liquid supply bag and the liquid flowing therefrom.

11. The apparatus of claim 10, wherein said humidifier cartridge further includes a float valve selectively exposing said interior chamber to said feed liquid supply bag and the liquid flowing therefrom.

12. A cartridge humidifier apparatus for use with a breathable gas supply and a separate heating unit, and, when engaged with the heating unit, the apparatus being adapted for heating and humidifying the breathable gas to be inhaled by a patient, the apparatus comprising:
 a feed water supply bag;
 a humidifier cartridge having a top portion and configured to operationally engage the heating unit to receive heat therefrom, the humidifier cartridge including a gas inlet, a humidified gas outlet, a water inlet adapted to receive water from said feed water supply bag, and an air outlet positioned in said top portion; and
 at least one air pressure equalizing conduit in fluid communication with said humidifier cartridge and said feed water supply bag for equalizing air pressure between said humidifier cartridge and said feed water supply bag.

13. The apparatus of claim 12, wherein said air outlet is at or above said water inlet.

14. The apparatus of claim 12, further comprising a heating unit having a base plate configured for being sealingly engaged to a lower end of said humidifier cartridge, said base plate including an insulating portion and a conductive portion.

15. The apparatus of claim 12, further comprising a securing sleeve connectable to said feed water supply bag and said at least one air pressure equalizing conduit and having a shoulder adjacent said feed water supply bag to facilitate connection of said at least one air pressure equalizing conduit to said feed water supply bag.

16. The apparatus of claim 15, further comprising a piercing pin configured for having an end of said piercing pin passing through said securing sleeve to connect to said feed water supply bag and another end connecting to said at least one air pressure equalizing conduit.

17. The apparatus of claim 16, wherein said piercing pin abuts against said shoulder of said securing sleeve upon said connection of said at least one air pressure equalizing conduit to said feed water supply bag.

18. The apparatus of claim 12, wherein said at least one air pressure equalizing conduit equalizes air pressure continuously between said humidifier cartridge and said feed water supply bag.

19. The apparatus of claim 12, the humidifier cartridge having a thermally conductive plate disposed opposite the top portion, the apparatus further comprising a heating unit have a heating surface adapted to thermally and physically engage the plate of the humidifier cartridge.

20. The apparatus of claim 12, wherein said humidifier cartridge further includes an interior chamber adapted to hold liquid, said interior chamber being selectively exposed to said feed water supply bag and the water flowing therefrom.

21. The apparatus of claim 20, wherein said humidifier cartridge further includes a float-valve selectively exposing said interior chamber to said feed water supply bag and the water flowing therefrom.

22. A humidifier apparatus for use in a respiratory therapy circuit having a breathable gas supply and operating at an air pressure, the apparatus comprising:
 a humidifier cartridge having a top and a bottom;
 a feed liquid supply bag having an upper end and a lower end, the feed liquid supply bag being held at an elevation such that the supply bag lower end is higher than the top of the humidifier cartridge;
 a first feed line fluidicly coupling the supply bag lower end into the humidifier cartridge such that liquid is able to flow from the supply bag into the humidifier cartridge; and
 a second feed line fluidicly coupling the upper end of the supply bag into the humidifier cartridge such that air pressure may be equalized between the supply bag and the humidifier cartridge.

23. The humidifier apparatus of claim 22, the first feed line being connected directly to the lower end of the supply bag.

24. The humidifier apparatus of claim 23, the humidifier cartridge having a water access aperture through the top thereof, the first feed line being connected directly to the water access aperture.

25. The humidifier apparatus of claim 22, the humidifier cartridge having an air access aperture through the top which couples into the humidifier cartridge, the second feed line being connected directly to the air access aperture.

26. The humidifier apparatus of claim 25, the supply bag having a second air access aperture adjacent the upper end, the second feed line being directly connected to the second air access aperture.

27. The humidifier apparatus of claim 25, the supply bag including an integral air return line portion extending from adjacent the upper end of the supply bag towards the lower end of the supply bag, the second feed line being connected to the integral air return line portion remote from the upper end of the supply bag.

28. The humidifier apparatus of claim 27, the integral air return line portion extending along a side of the supply bag between the upper end and lower end, and terminating in a second air access aperture, the second feed line being connected directly to the second air access aperture.

29. The humidifier apparatus of claim 22, the supply bag having an air access aperture adjacent the upper end, the second feed line being directly connected to the air access aperture.

30. The humidifier apparatus of claim 22, the supply bag including an integral air return line portion extending from adjacent the upper end of the supply bag towards the lower end of the supply bag, the second feed line being connected to the integral air return line portion remote from the upper end of the supply bag.

31. The humidifier apparatus of claim 30, the integral air return line portion extending along a side of the supply bag between the upper end and lower end, and terminating in an air access aperture, the second feed line being connected directly to the air access aperture.

32. The humidifier apparatus of claim 22, further comprising a heating unit having an upper heating surface adapted to thermally engage the bottom of the humidifier cartridge.

33. The humidifier apparatus of claim 22, the first and second feed lines being physically connected to each other along at least a portion of their length.

34. The apparatus of claim 22, wherein the humidifier cartridge further includes an interior chamber adapted to hold liquid, the interior chamber being selectively exposed to the first feed line and the liquid flowing therein.

35. The apparatus of claim 34, wherein the humidifier cartridge further includes a float valve selectively exposing the interior chamber to the first feed line and the liquid flowing therein.

36. A humidifier apparatus for use in a respiratory therapy circuit having a breathable gas supply and operating at an air pressure, the apparatus comprising:
   a humidifier cartridge;
   a feed liquid supply bag having an upper end and a lower end, the supply bag including an integral air return line portion extending from adjacent the upper end of the supply bag towards the lower end of the supply bag;
   a first feed line fluidicly coupling the lower end of the supply bag to the humidifier cartridge such that liquid is able to flow from the supply bag into the humidifier cartridge; and
   a second feed line connected to the integral air return line portion remote from the upper end of the supply bag and fluidicly coupling the integral air return line portion to the humidifier cartridge such that air pressure may be equalized between the supply bag and the humidifier space.

37. The humidifier apparatus of claim 36, the integral air return line portion extending along a side of the supply bag between the upper end and lower end, and terminating in an air access aperture, the second feed line being connected directly to the air access aperture.

38. A humidifier apparatus for use in a respiratory therapy circuit having a breathable gas supply and operating at an air pressure, the apparatus comprising:
   a feed liquid supply bag;
   a humidifier cartridge;
   a first feed line fluidicly coupling a lower end of the supply bag to the humidifier cartridge such that liquid is able to flow from the supply bag into the humidifier cartridge; and
   a second, unobstructed feed line fluidicly coupling an upper end of the supply bag to the humidifier cartridge such that air pressure may be equalized between the supply bag and the humidifier cartridge.

39. The apparatus of claim 38, wherein the humidifier cartridge further includes an interior chamber adapted to hold liquid, the interior chamber being selectively exposed to the first feed line and the liquid flowing therein.

40. The apparatus of claim 39, wherein the humidifier cartridge further includes a float valve selectively exposing the interior chamber to the first feed line and the liquid flowing therein.

* * * * *

UNITED STATES PATENT AND TRADEMARK OFFICE
CERTIFICATE OF CORRECTION

PATENT NO. : 6,988,497 B2
DATED : January 24, 2006
INVENTOR(S) : Levine

It is certified that error appears in the above-identified patent and that said Letters Patent is hereby corrected as shown below:

Column 6,
Line 52, "said feed liquid bag" should read -- said feed liquid supply bag --.

Column 7,
Line 19, "adapted to bold liquid" should read -- adapted to hold liquid --.

Column 8,
Line 16, "includes a float-valve selectively" should read -- includes a float valve selectively --.

Signed and Sealed this

Sixteenth Day of May, 2006

JON W. DUDAS
*Director of the United States Patent and Trademark Office*